United States Patent
Yoo et al.

(10) Patent No.: US 7,531,147 B2
(45) Date of Patent: May 12, 2009

(54) METHOD OF PRODUCING UNSATURATED ALDEHYDE AND/OR UNSATURATED ACID

(75) Inventors: Yeon Shick Yoo, Naju-si (KR); Hyun Jong Shin, Gwangju (KR); Byung Yul Choi, Naju-si (KR); Young Hyun Choi, Jeollanam-do (KR); Young Jin Cho, Naju-si (KR); Duk Ki Kim, Gwangju (KR); Joo Yeon Park, Gwangju (KR); Kwang Ho Park, Daejeon (KR)

(73) Assignee: LG Chem, Ltd. (KR)

( * ) Notice: Subject to any disclaimer, the term of this patent is extended or adjusted under 35 U.S.C. 154(b) by 34 days.

(21) Appl. No.: 11/362,978

(22) Filed: Feb. 27, 2006

(65) Prior Publication Data
US 2006/0211885 A1 Sep. 21, 2006

(30) Foreign Application Priority Data
Feb. 25, 2005 (KR) .................. 10-2005-0015927

(51) Int. Cl.
*B01J 19/00* (2006.01)
*B01J 8/08* (2006.01)
*B01J 35/02* (2006.01)
*B01J 21/00* (2006.01)

(52) U.S. Cl. .............. 422/198; 422/188; 422/190; 422/191; 422/193; 422/211; 422/213; 422/216; 422/221; 422/222; 502/84; 502/100

(58) Field of Classification Search .......... 422/188, 422/190, 193, 198, 201, 211, 221, 213, 216, 422/191, 222; 502/84, 100; 208/11.05, 210, 208/213, 326, 66, 74, 134, 143, 146, 165, 208/169, 250, 208 R; 585/265, 653, 654, 585/648, 660
See application file for complete search history.

(56) References Cited

U.S. PATENT DOCUMENTS 3,617,510 A * 11/1971 Hayes .................. 208/111.05
(Continued)

FOREIGN PATENT DOCUMENTS

JP 53030688 3/1978
(Continued)

OTHER PUBLICATIONS

JP4324403; Tadao, et al; "Method For Removing Coating of Coated Optical Fiber"; Nov. 13, 1992; Abstract only; 1 page.
(Continued)

*Primary Examiner*—Walter D Griffin
*Assistant Examiner*—Huy-Tram Nguyen
(74) *Attorney, Agent, or Firm*—Cantor Colburn LLP

(57) ABSTRACT

Disclosed is a shell-and-tube reactor that may be used for fixed-bed catalytic partial oxidation, the reactor being characterized by including at least one reaction zone of a first-step reaction zone for mainly producing unsaturated aldehydes and a second-step reaction zone for mainly producing unsaturated acids, wherein at least one reaction zone of the above reaction zones comprises two or more catalytic layers; each of the catalytic layers is packed with a formed product of catalyst that is different in pore density and/or pore size in a catalytically active component; and the pore density and/or pore size is controlled in such a manner that specific surface area of the catalytically active component increases from the inlet of the reactor to the outlet of the reactor. A method for producing unsaturated aldehydes and/or unsaturated fatty acids from olefins using the same reactor is also disclosed. According to the present invention, it is possible to control the temperature efficiently at a hot spot, thereby permitting stable use of a catalyst, and to produce unsaturated aldehydes and/or unsaturated fatty acids with high yield.

11 Claims, 1 Drawing Sheet

U.S. PATENT DOCUMENTS

| | | | | |
|---|---|---|---|---|
| 3,696,027 A * | 10/1972 | Bridge | ................ | 208/210 |
| 3,966,644 A * | 6/1976 | Gustafson | ................ | 502/66 |
| 4,306,964 A * | 12/1981 | Angevine | ................ | 208/210 |
| 4,327,190 A * | 4/1982 | Ball et al. | ................ | 518/714 |
| 4,332,971 A * | 6/1982 | Dalton et al. | ................ | 568/480 |
| 4,421,633 A * | 12/1983 | Shih et al. | ................ | 208/59 |
| 4,720,477 A * | 1/1988 | Hettinger, Jr. | ................ | 502/255 |
| 4,789,462 A * | 12/1988 | Byrne et al. | ................ | 208/213 |
| 4,810,685 A * | 3/1989 | Twigg et al. | ................ | 502/60 |
| 4,830,736 A * | 5/1989 | Hung et al. | ................ | 208/251 H |
| 4,837,360 A * | 6/1989 | Kadowaki et al. | ................ | 562/546 |
| 5,048,601 A | 9/1991 | Yamaguchi et al. | | |
| 5,072,052 A * | 12/1991 | Boeck et al. | ................ | 568/479 |
| 5,198,581 A | 3/1993 | Kawajiri et al. | | |
| 5,233,118 A * | 8/1993 | Bricker et al. | ................ | 585/660 |
| 5,344,553 A * | 9/1994 | Shih | ................ | 208/49 |
| 6,069,271 A | 5/2000 | Tanimoto et al. | | |
| 6,124,234 A * | 9/2000 | Fetzer et al. | ................ | 502/326 |
| 6,303,531 B1 * | 10/2001 | Lussier et al. | ................ | 502/84 |
| 6,399,818 B2 | 6/2002 | Tanimoto et al. | | |
| 6,657,080 B2 | 12/2003 | Yunoki | | |
| 6,781,013 B2 * | 8/2004 | Tanimoto | ................ | 562/532 |
| 6,960,684 B2 * | 11/2005 | Yunoki | ................ | 562/547 |
| 2002/0007088 A1 | 1/2002 | Tanimoto et al. | | |
| 2004/0054222 A1 | 3/2004 | Felder et al. | | |
| 2006/0247446 A1 * | 11/2006 | Neto et al. | ................ | 549/249 |

FOREIGN PATENT DOCUMENTS

| | | |
|---|---|---|
| JP | 2000336060 | 12/2000 |
| KR | 1020000077433 A1 | 12/2000 |
| RU | 1806834 A1 * | 4/1993 |

OTHER PUBLICATIONS

International Search Report; International Application No. PCT/KR2006/000596; International Filing Date Feb. 22, 2006; Applicant's File Reference No. FPC06008-PCT; Date of Mailing Apr. 27, 2006; 3 pages.

Taiwan Office Action; Application No. 095105943; Dated Dec. 25, 2008.

* cited by examiner

METHOD OF PRODUCING UNSATURATED ALDEHYDE AND/OR UNSATURATED ACID

This application claims the benefit of the filing date of Korean Patent Application No. 2005-15927, filed on Feb. 25, 2005, in the Korean Intellectual Property Office, the disclosure of which is incorporated herein in its entirety by reference.

TECHNICAL FIELD

The present invention relates to a method for producing unsaturated aldehydes and/or unsaturated acids from olefins by means of fixed-bed catalytic partial oxidation in a shell-and-tube heat exchange type reactor, as well as to a fixed-bed shell-and-tube heat exchange type reactor used in the above method.

BACKGROUND ART

A process for producing unsaturated aldehydes and/or unsaturated acids from $C_3$~$C_4$ olefins by using a catalyst is a typical example of catalytic vapor phase oxidation.

Particular examples of catalytic vapor phase oxidation include a process for producing acrolein and/or acrylic acid by oxidizing propylene or propane, a process for producing methacrolein and/or methacrylic acid by oxidizing isobutylene, t-butyl alcohol or methyl t-butyl ether, or the like.

(Meth)acrylic acid, which is an unsaturated acid, is a material useful for various applications including coating agents, adhesives, plasticizers and various kinds of synthetic resins.

In general, catalytic vapor phase oxidation is implemented as follows. At least one catalyst in the form of granules is packed into reaction tubes, feed gas 1 is supplied to a reactor through the reaction tubes and the feed gas is in contact with the catalyst in the reaction tubes to perform vapor phase oxidation. Reaction heat generated during the reaction is removed by heat transfer with a heat transfer medium, wherein the temperature of the heat transfer medium is maintained at a predetermined temperature. Herein, the heat transfer medium for heat exchange is provided on the outer surface of the reaction tubes to perform heat transfer. A reaction mixture 3 containing a desired product is collected via a duct and then sent to a purification step. Generally, catalytic vapor phase oxidation is a highly exothermic reaction. Therefore, it is very important to control the reaction temperature in a specific range and to downsize hot spots in the reaction zone.

To perform the partial oxidation of propylene, propane, isobutylene, t-butyl alcohol or methyl t-butyl ether (also referred to as 'propylene or the like' hereinafter), a multimetal oxide containing molybdenum and bismuth or vanadium or a mixture thereof is used as a catalyst.

Generally, propylene or the like is subjected to two-step catalytic vapor phase partial oxidation to produce (meth)acrylic acid as a final product. More particularly, in the first step 10, propylene or the like is oxidized by oxygen, diluted inert gas, water vapor and an optional amount of catalyst to produce (meth)acrolein 2 as a main product. In the second step 20, (meth)acrolein obtained from the preceding step is oxidized by oxygen, diluted inert gas, water vapor and an optional amount of catalyst to produce (meth)acrylic acid 3. The catalyst used in the first step is an oxidation catalyst based on Mo—Bi, which oxidizes propylene or the like to provide (meth)acrolein as a main product. Additionally, a part of (meth)acrolein is further oxidized on the same catalyst to form acrylic acid partially. The catalyst used in the second step is an oxidation catalyst based on Mo—V, which oxidizes (meth)acrolein-containing mixed gas produced in the first step, particularly (meth)acrolein, to provide (meth)acrylic acid as a main product.

Reactors for carrying out the above process are realized in such a manner that each of the above two steps are implemented in one system or in two different systems (FIG. 1).

Meanwhile, many attempts have been made to increase productivity of the reactor for producing acrylic acid by modifying the reactor structure, by suggesting an optimized catalyst for oxidation or by improving the operational conditions.

As mentioned above, vapor phase oxidation of propylene or the like, or (meth)acrolein is an exothermic reaction. Therefore, there is a problem in that a hot spot (a point whose temperature is abnormally high or where heat accumulation is relative high) is generated in a catalytic bed in the reactor. Such hot spots show a relatively high temperature compared to other parts of the reactor. Accordingly, in hot spots, complete oxidation proceeds rather than partial oxidation, thereby increasing production of by-products such as COx, and decreasing the yield of (meth)acrolein or (meth)acrylic acid. Further, exposure of catalyst to high temperature causes rapid inactivation of catalyst, thereby shortening the lifetime of catalyst. To solve these problems, a method for inhibiting generation of hot spots and equalizing the availability of catalyst over the whole reactor has been studied to obtain (meth)acrolein or (meth)acrylic acid with high yield and to use the catalyst for a long period of time. In this regard, many improved catalysts have been continuously suggested.

For example, Japanese Laid-Open Patent Nos. Sho43-24403 and Sho53-30688 disclose a method for packing a catalytic bed by diluting a catalyst with an inactive material in a stepwise manner from the inlet of feed gas to the outlet of feed gas. However, the above method has a problem in that it takes too much time and is very difficult to pack the catalytic bed while varying the dilution ratio with an inactive material from 100% to 0% gradually. In addition, Korean Laid-Open Patent No. 2000-77433 and Japanese Laid-Open Patent No. 2000-336060 disclose a method for using multiple kinds of catalysts formed by varying the kind and amount of alkali metals. However, the method has difficulty in producing catalysts having different activities at a correct ratio because the amount of alkali metal used therein is small.

Further, Korean Laid-Open Patent No. 1995-4027 discloses a method of packing a catalyst in such a manner that the catalyst particles have a relatively large size in the vicinity of a hot spot. However, in this case, such catalyst particles having a large size may cause occlusion of a reaction tube or may have insufficient activity. Thus, there is a problem in that it is not possible to obtain conversion of propylene or isobutylene and yield of (meth)acrylic acid to a desired degree.

Therefore, there is a continuous need to develop a method for producing unsaturated aldehydes and/or unsaturated fatty acids with high yield while permitting stable use of a catalyst, by controlling the temperature of the highest-temperature hot spot efficiently.

DISCLOSURE OF THE INVENTION

It is an object of the present invention to provide a method for producing unsaturated aldehydes and/or unsaturated fatty acids with high yield while permitting stable use of a catalyst, by controlling the temperature of a hot spot efficiently, wherein the method is performed in a reactor having a first reaction zone 11 for mainly producing unsaturated aldehydes (for example, (meth) acrolein) and a second reaction zone 21 for mainly producing unsaturated acids (for example, (meth)

acrylic acid); at least one reaction zone of the first and the second reaction zones is packed with two or more catalytic layers, thereby dividing the reaction zone(s) into two or more reaction regions; and a formed product of catalyst packed in each of the catalytic layers is different in pore density and/or pore size in a catalytically active component, and the pore density and/or size in the catalytically active component is controlled in such a manner that the specific surface area of the catalytically active component gradually increases from the reaction zone at the inlet of the reactor to the reaction zone at the outlet of the reactor.

According to an aspect of the present invention, there is provided a shell-and-tube reactor that may be used for fixed-bed catalytic partial oxidation, the reactor being characterized by including at least one reaction zone of a first-step reaction zone for mainly producing unsaturated aldehydes and a second-step reaction zone for mainly producing unsaturated acids, wherein at least one reaction zone of the above reaction zones comprises two or more catalytic layers; each of the catalytic layers is packed with a formed product of catalyst that is different in pore density and/or pore size in the catalytically active component; and the pore density and/or pore size is controlled in such a manner that the specific surface area of the catalytically active component increases from the inlet of the reactor to the outlet of the reactor.

According to another aspect of the present invention, there is provided a method for producing unsaturated aldehydes from olefins by means of fixed-bed catalytic partial oxidation in a shell-and-tube reactor, the method being characterized in that the reactor includes a reaction zone for producing unsaturated aldehydes, which comprises two or more catalytic layers, wherein each of the catalytic layers is packed with a formed product of catalyst that is different in pore density and/or pore size in a catalytically active component; and the pore density and/or pore size is controlled in such a manner that the specific surface area of the catalytically active component increases from the inlet of the reactor to the outlet of the reactor.

According to still another aspect of the present invention, there is provided a method for producing unsaturated acids from unsaturated aldehydes by means of fixed-bed catalytic partial oxidation in a shell-and-tube reactor, the method being characterized in that the reactor includes a reaction zone for producing unsaturated acids, which comprises two or more catalytic layers, wherein each of the catalytic layers is packed with a formed product of catalyst that is different in pore density and/or pore size in a catalytically active component; and the pore density and/or pore size is controlled in such a manner that the specific surface area of the catalytically active component increases from the inlet of the reactor to the outlet of the reactor.

Hereinafter, the present invention will be explained in detail.

Preferably, the olefin, unsaturated aldehyde and unsaturated acid compounds have 3-4 carbon atoms, and include propylene or isobutylene, (meth)acrolein and (meth)acrylic acid, respectively. Additionally, it is possible to use propane, t-butyl alcohol, methyl t-butyl ether or a mixture thereof, as a starting material for producing unsaturated aldehydes or unsaturated acids, in the scope of the present invention.

Preferably, the catalytically active component in the formed product of catalyst used in the first-step reaction zone for mainly producing unsaturated aldehydes is a metal oxide represented by the following formula 1:

$$Mo_a A_b B_c C_d D_e E_f F_g O_h$$ [formula 1]

wherein Mo is molybdenum;
A is at least one element selected from the group consisting of Bi and Cr;
B is at least one element selected from the group consisting of Fe, Zn, Mn, Nb and Te;
C is at least one element selected from the group consisting of Co, Rh and Ni;
D is at least one element selected from the group consisting of W, Si, Al, Zr, Ti, Cr, Ag and Sn;
E is at least one element selected from the group consisting of P, Te, As, B, Sb, Sn, Nb, Cr, Mn, Zn, Ce and Pb;
F is at least one element selected from the group consisting of Na, K, Li, Rb, Cs, Ta, Ca, Mg, Sr, Ba and MgO; and
each of a, b, c, d, e, f and g represents the atomic ratio of each element, with the proviso that when a=10, b is a number of 0.01~10, c is a number of 0.01~10, d is a number of 0.0~10, e is a number of 0.0~10, f is a number of 0~20, g is a number of 0~10, and h is a number defined depending on the oxidation state of each of the above elements.

Preferably, the catalytically active component in the formed product of catalyst used in the second-step reaction zone for mainly producing unsaturated acids is a metal oxide represented by the following formula 2:

$$Mo_a W_b V_c A_d B_e C_f O_x$$ [formula 2]

wherein Mo is molybdenum;
W is tungsten;
V is vanadium;
A is at least one element selected from the group consisting of iron (Fe), copper (Cu), bismuth (Bi), chrome (Cr), cobalt (Co) and manganese (Mn);
B is at least one element selected from the group consisting of tin (Sn), antimony (Sb), nickel (Ni), cesium (Cs) and thallium (Tl);
C is at least one element selected from the group consisting of alkali metals and alkaline earth metals;
O is an oxygen atom; and
each of a, b, c, d, e, f and x represents the atomic ratio of Mo, W, V, A, B, C and O atoms, with the proviso that when a=10, 0.5≦b≦4, 0.5≦c≦5, 0≦d≦5, 0≦e≦2, 0≦f≦2, and x is a number defined depending on the oxidation state of each of the above elements.

The formed product of catalyst may be obtained by forming metal oxide powder or a precursor thereof through an extrusion process or a pelletizing process and baking the resultant product. Otherwise, it may be obtained by coating metal oxide or a precursor thereof in a liquid or powder state onto an inactive carrier and baking the resultant product.

As used herein, the term "pore density" means the number of pores produced by a sublimable or thermally decomposable material per unit volume.

One embodiment of the method for preparing a catalytically active component having a different pore density and/or pore size comprises the steps of:

(a) mixing metal salts forming a metal oxide to provide an aqueous solution or suspension of catalyst;

(b) drying the aqueous solution or suspension of catalyst to provide catalyst powder; and (c) baking the resultant product obtained from the preceding step, the method further comprising a step of adding a sublimable or thermally decomposable material, which has a controlled addition amount and/or a controlled particle size, during step (a) or between step (b) and step (c).

In the method for preparing the catalyst used in the present invention, the baking step is performed at a temperature ranging from room temperature to 500° C. while increasing the temperature gradually. In general, it is known that each metal element forming the catalytically active component undergoes a structural change at a temperature of 200° C. or higher.

Herein, addition of the sublimable or thermally decomposable material during the preparation of the catalyst causes heat emission to a certain degree. Since sublimation or thermal decomposition of each additive, performed at a temperature of 200° C. or higher, may cause undesired heat emission and an undesired structural change in a metal, it is preferable that the sublimable or thermally decomposable material is sublimed or thermally decomposed at a temperature of 50° C.~200° C. Particular examples of such sublimable or thermally decomposable materials include urea ($NH_2CONH_2$), melamine ($C_3H_6N_6$), ammonium oxalate ($C_2H_8N_2O_4$), methyl oxalate ($C_4H_6O_4$) and naphthalene ($C_{10}H_8$).

Particularly, it is preferable that the thermally decomposable material evaporates in a gas state after its thermal decomposition.

There is no particular limitation in the metal salt, forming the metal oxide represented by the above formula 1 or 2, when preparing the aqueous solution or suspension of catalyst. Particular examples of the salt that may be used include nitrate, acetate, carbonate, organic acid salts, ammonium salts, hydroxides and oxides.

According to the present invention, it is possible to control the pore density and/or pore size of the catalytically active component in a finally formed product of catalyst by controlling either or both of the addition amount and particle size of the sublimable or thermally decomposable material.

It is currently known that a commercially available catalyst for producing unsaturated aldehydes and/or unsaturated acids comprising a multimetal oxide has a small specific surface area. Such catalysts show a small contact area to a reactant material, and thus show low catalytic activity. Also, it is not possible to control the specific surface area of the catalytically active component efficiently. According to the present invention, a sublimable or thermally decomposable material is used as an additive during the preparation of a catalyst and the particle size and/or the amount of the sublimable or thermally decomposable material is controlled, so that the pore density and/or pore size in the catalytically active component in the finally formed product of catalyst can be controlled. Therefore, it is possible to control the specific surface area of the catalyst with ease, and thus to provide catalysts with high efficiency and different activities.

The sublimable or thermally decomposable material having a small number of carbon atoms, such as urea ($NH_2CONH_2$), melamine ($C_3H_6N_6$), ammonium oxalate ($C_2H_8N_2O_4$), methyl oxalate ($C_4H_6O_4$) or naphthalene ($C_{10}H_8$), occupies a certain amount of volume in the catalyst composition while the catalyst is formed. Then, the sublimable or thermally decomposable material is removed by drying or baking it at a relatively low temperature, thereby forming pores in the catalytically active component. When the amount and particle size of the sublimable or thermally decomposable material are controlled, it is possible to control the specific surface area of the catalytically active component to an adequate degree. Meanwhile, as the specific surface area of the catalytically active component increases, the catalyst shows higher activity. On the other hand, as the specific surface area of the catalytically active component decreases, the catalyst shows lower activity.

The sublimable or thermally decomposable material may be used in the form of granular powder or in a liquid state. When the material is used in the form of granular powder, it preferably has a particle size of 0.01~50 μm. More preferably, the sublimable or thermally decomposable material has a particle size of 0.01~10 μm.

The sublimable or thermally decomposable material is used in an amount of 0~30 wt % based on the weight of the catalyst formed of the compound represented by the above formula 1. The material is suitably used in an amount of 0.1~20 wt % in order to ensure the quality and durability of the resultant catalyst. The sublimable or thermally decomposable material is used in an amount of 0~30 wt % based on the weight of the catalyst formed of the compound represented by the above formula 2. The material is used suitably in an amount of 0.1~20 wt % in order to ensure the quality and durability of the resultant catalyst. When a carrier is used, the material is used preferably in an amount reduced according to the ratio of the amount of precursor of catalytically active component to the amount of carrier.

There is no particular limitation in the time of the addition of the sublimable or thermally decomposable material. The sublimable or thermally decomposable material may be added during the preparation of the liquid catalytically active component (aqueous solution or suspension of catalyst), or may be mixed with dried catalytically active component present in the form of powder. However, it is preferable that the sublimable or thermally decomposable material is added right before the step of forming (for example, extruding, pelletizing or coating) the catalyst in order to control the specific surface area of the formed product of catalyst as correctly as possible.

Additionally, it is possible to further carry out a pretreatment step, wherein the pulverized catalyst powder is baked under oxygen atmosphere at 180~250° C. for 3~5 hours, before the sublimable or thermally decomposable material is added to the catalyst powder. This is because such pretreatment removes a nitrate compound having hygroscopic property before the catalyst is formed, and thus improves the workability.

Preferably, the catalyst powder used in the process for producing the formed product of catalyst is pulverized into a particle size of 150 μm or less, in order to produce the formed product of catalyst smoothly.

Further, there is no particular limitation in temperature during the baking step in the process for producing the formed product of catalyst according to the present invention. Generally, the formed product of catalyst, which is obtained by a direct extrusion process or pelletizing process of a catalytically active component, or by coating a catalytically active component onto an inert carrier, may be used before baking it at a temperature of 500° C. or less for 5~20 hours. The baking temperature of the formed products in each of the reaction zones may be the same or different.

There is no particular limitation in the shape of the formed product of catalyst. The formed product of catalyst may have a cylindrical shape, a spherical shape, a pellet-like shape or a ring-like shape. The catalytically active component may be formed by using a conventional catalyst forming method, such as a direct extrusion method or a pelletizing method. Otherwise, the catalytically active component may be coated onto an inert carrier, such as alundum, silica-alumina or silicon carbide. Preferably, the formed product of catalyst has a cylindrical shape or a hollow cylindrical shape. However, when a final catalyst is prepared by using a catalytically active component alone, the catalyst may have undesirably high activity. Thus, in this case, it is preferable that the catalyst has a hollow ring-like shape. For example, it is advisable that the catalyst has a cylindrical shape having a diameter of 3~8 mm in which a cavity having a diameter of about 0.5~5 mm is perforated, so that the content of catalytically active component can be 20~70%. When a catalytically active component, present in a liquid state or in the form of dry powder, is supported on a carrier, it is preferable that the catalytically active component is coated in a rotary coater, a centrifugal coater or a spherudizer. When the catalytically active component is coated onto a carrier, it is advisable that the catalytically active component is supported on a spherical carrier in an amount of 20~70% and formed into particles having a size of 3~8 mm in order to facilitate forming and packing of the catalyst.

The present invention is characterized in that a plurality of formed products of catalyst having a different pore density and/or pore size in the catalytically active component are packed into each of the zones formed by dividing a reaction tube in a reactor into multiple zones.

Further, the present invention is characterized in that the pore density and/or pore size in the catalytically active component is controlled in such a manner that the specific surface area of the catalytically active component increases from the inlet of the reactor to the outlet of the reactor.

To increase the specific surface area of the catalytically active component, it is possible to increase the pore density, to increase the pore size, or to increase both of the pore density and the pore size. However, even if one of the pore density and the pore size is increased and the other is decreased, it is possible to increase the specific surface area of the catalytically active component. Thus, this is also included in the scope of the present invention. Meanwhile, one embodiment of the present invention, wherein the specific surface area of the catalytically active component is the smallest, includes the catalytically active component having no pores.

A hot spot is referred to as a point whose temperature is abnormally high or where heat accumulation is high, in a catalytic bed. In general, in the case of the first-step reaction zone, the highest-temperature hot spot is generated at the front part of the first-step reaction zone, enriched with olefins (e.g., propylene or the like) as a main reactant and molecular oxygen. Similarly, in the case of the second-step reaction zone, the highest-temperature hot spot is generated at the front part of the second-step reaction zone, enriched with unsaturated aldehydes (e.g., (meth)acrolein) and molecular oxygen. Additionally, as the pore density and/or the pore size of the catalytically active component increases, the catalyst shows increased reactivity (while showing decreased selectivity and stability). Therefore, it is possible to reduce heat generation and to prevent excessive heat accumulation, and thus to prevent production of undesired byproducts, by packing a catalytic layer having the smallest pore density and/or pore size of the catalytically active component in the vicinity of the front part of the each of the first-step reaction zone and the second-step reaction zone. Additionally, it is possible to increase the activity in the rear end part of the reaction tube, to increase the total yield of a desired product, and to produce the final product stably for a long period of time, by packing catalytic layers having a relatively large pore density and/or pore size serially from the part following the hot-spot to the rear end part.

According to the present invention, it is possible to control the catalytic activity while maintaining the uniform size of a catalyst, not by controlling the size (volume) of the catalyst itself but by controlling the pore size and/or density in the catalytically active component. Additionally, according to the present invention, the micropores in the catalytically active component form a flow path for the reactants and serve to dissipate the reaction heat, thereby preventing undesirably excessive heat emission. Therefore, it is possible to provide excellent selectivity while maintaining an excellent conversion ratio.

Further, since it is possible to control the pore size and/or pore density in a continuous manner as well as in a discontinuous manner, various catalytic layers comprising catalytically active components having a different pore size and/or pore density can be packed into the reaction zone.

Theoretically, when the number of reaction zones increases, the reaction zones being divided through the use of different catalytic layers in the first step and the second step depending on the exothermic temperature distribution of the reactor, it is possible to control the reaction heat more easily. However, it is not possible to increase the number of reaction zones infinitely when seen from a commercial point of view. Therefore, in order to satisfy the effect of the present invention to a desired degree, it is preferable to use reaction zones with two or three levels. Meanwhile, each catalytic layer may be packed to any height capable of controlling the heat generation of the reactor efficiently. The packing height of the catalytic layer having the smallest specific surface area of the catalytically active component by controlling the pore density and/or pore size preferably includes the highest-temperature hot spot. More particularly, the above-mentioned packing height, starting from the inlet, is 10~50%, preferably 10~30% of the total height of the catalytic bed.

When controlling the specific surface area of the catalytically active component by the pore size and/or pore density of a catalytically active component used in each level of the reactor, for example, when preparing a catalyst having a relatively large specific surface area of the catalytically active component (the catalyst being used in the second or the third level following the hot spot), it is preferable to add a sublimable material or a thermally decomposable material in such a manner that the amount and/or the particle size of the material increases gradually from 1 to 3 folds, as compared to that of a catalyst having a relatively small specific surface area of the catalytically active component (the catalyst being used in the vicinity of the hot spot).

When different catalytic layers are packed in two levels, in the first-step reaction zone and/or the second-step reaction zone, it is preferable that the catalytically active component in the first level has a specific surface area of 5~10 m$^2$/g, and the catalytically active component in the second level has a specific surface area of 10~100 m$^2$/g.

Additionally, when different catalytic layers are packed in three levels, in the first-step reaction zone and/or the second-step reaction zone, it is preferable that the catalytically active component in the first level has a specific surface area of 5~10 m$^2$/g, the catalytically active component in the second level has a specific surface area of 10~50 m$^2$/g, and the catalytically active component in the third level has a specific surface area of 50~100 m$^2$/g.

There is no particular limitation in the reaction condition used in the present invention. In the present invention, it is possible to introduce any reaction conditions known to be useful for producing acrolein and acrylic acid via vapor phase catalytic oxidation of propylene or propane or for producing methacrolein and methacrylic acid via vapor phase catalytic oxidation of isobutylene, t-butyl alcohol and methyl t-butyl ether, in a fixed-bed multi-tube type shell-and-tube reactor. For example, in order to perform oxidation in a reactor according to the present invention, a feed gas including 1~10 volume % of a feed compound such as propylene, 1~15 volume % of molecular oxygen, 5~60 volume % of water vapor and 20~80 volume % of an inert gas (wherein the total volume of the above components is 100 volume %) is introduced onto a catalyst at a temperature ranging from 200° C. to 350° C., under a pressure of between atmospheric pressure and 3 atm, at a space velocity of 500~4000 hr$^{-1}$ (STP).

MODE FOR CARRYING OUT THE INVENTION

Figure 1:
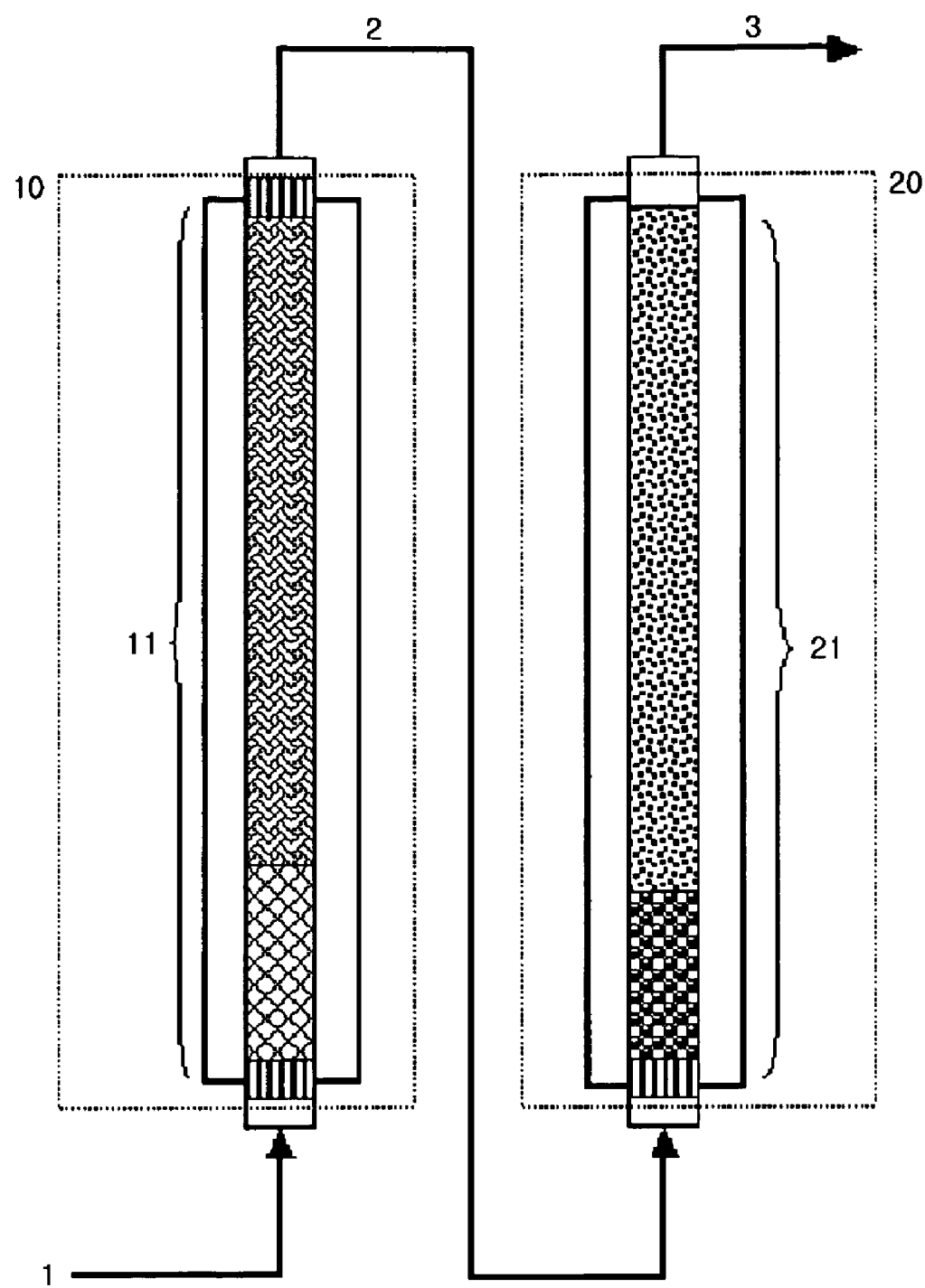
FIG. 1 is a schematic view showing the structure of a pilot reactor, wherein the first-step reaction and the second-step reaction are performed individually in a different reactor, each reactor comprising one catalytic tube, and the structure of a catalytic bed disposed inside of the catalytic tube.

Reference will now be made in detail to the preferred embodiments of the present invention. It is to be understood that the following examples are illustrative only and the present invention is not limited thereto.

PREPARATION EXAMPLE (Preparation of Catalyst 1)

To a 50 L glass reactor equipped with a branch type agitator, 30 L of distilled water was introduced and then heated. At 90° C., 10,000 g of ammonium molybdate was dissolved therein to form solution (1). To 2500 ml of distilled water, 6593 g of cobalt nitrate, 4121 g of bismuth nitrate, 2746 g of iron nitrate, 185 g of cerium nitrate, 258 g of manganese nitrate and 28.63 g of potassium nitrate were added and then mixed thoroughly to form solution (2). While agitating solution (1) vigorously, solution (2) was introduced slowly into solution (1), to form catalyst suspension. After drying the catalyst suspension for at least 12 hours, it was pulverized into a size of 150 μm or less. Then, urea ($NH_2CONH_2$) was added thereto to an amount of 10 wt % based on the total weight (combined weight of the pulverized catalytically active component+urea). The resultant product was formed into ring-shaped pellets having an inner diameter of 2 mm, an outer diameter of 6 mm and a length of 6 mm. The pellets were baked at 450° C. under air for 5 hours and then checked for catalytic activity. The resultant catalytically active component had the composition of: $Mo_{10}Bi_{1.5}Fe_{1.2}Co_4K_{0.05}Ce_{0.1}Mn_{0.1}$ (Catalyst 1), excluding oxygen.

(Preparation of Catalyst 2)

The process described in the above Preparation of Catalyst 1 was repeated to provide Catalyst 2, except that urea ($NH_2CONH_2$) was used in an amount of 20 wt %. The resultant catalytically active component had the composition of: $Mo_{10}Bi_{1.5}Fe_{1.2}Co_4K_{0.05}Ce_{0.1}Mn_{0.1}$ (Catalyst 2) excluding oxygen.

(Preparation of Catalyst 3)

The process described in the above Preparation of Catalyst 1 was repeated to provide Catalyst 3, except that urea ($NH_2CONH_2$) was not added. The resultant catalytically active component had the composition of: $Mo_{10}Bi_{1.5}Fe_{1.2}Co_4K_{0.05}Ce_{0.1}Mn_{0.1}$ (Catalyst 3), excluding oxygen.

(Preparation of Catalyst 4)

The process described in the above Preparation of Catalyst 1 was repeated to provide Catalyst 4, except that naphthalene ($C_{10}H_8$) was added in an amount of 10 wt % instead of urea ($NH_2CONH_2$) and 622.5 g of aluminum chloride was added instead of cerium nitrate and manganese nitrate. The resultant catalytically active component had the composition of: $Mo_{10}Bi_{1.5}Fe_{1.2}Co_4Al_1K_{0.05}$ (Catalyst 4), excluding oxygen.

(Preparation of Catalyst 5)

The process described in the above Preparation of Catalyst 4 was repeated to provide Catalyst 5, except that naphthalene ($C_{10}H_8$) was added in an amount of 20 wt %. The resultant catalytically active component had the composition of: $Mo_{10}Bi_{1.5}Fe_{1.2}Co_4Al_1K_{0.05}$ (Catalyst 5), excluding oxygen.

(Preparation of Catalyst 6)

To a 50 L glass reactor equipped with a conventional branch type agitator and a homogenizer, 30 L of distilled water was introduced and then heated. When distilled water reached the boiling point, 2960 g of ammonium paratungstate, 10000 g of ammonium molybdate and 2320 g of ammonium metavanadate were introduced, in turn. The reaction mixture was heated to maintain the boiled state while agitating it to completely dissolve the compounds. Then, while the homogenizer was rotated at 4000 rpm, an aqueous solution containing 1370 g of copper nitrate, 1650 g of nickel nitrate and 960 g of strontium nitrate, dissolved in 2.6 L of water, was mixed with the above aqueous solution containing the mixed three ammonium salts. To the resultant suspension, urea ($NH_2CONH_2$) was added in an amount of 10 wt %. Then, the resultant catalyst suspension was coated onto a silica-alumina carrier having a diameter of 5 mm to obtain a catalyst. The catalyst supported on the carrier was baked for 5 hours at 450° C. under air to provide a final catalyst. After baking, the resultant catalyst was comprised of 30 wt % of catalyst powder based on the combined weight of the catalyst powder and the carrier. The resultant catalytically active component had the composition of: $Mo_{10}W_2V_{3.5}Cu_1Ni_1Sr_{0.8}$ (Catalyst 6), excluding oxygen.

(Preparation of Catalyst 7)

The process described in the above Preparation of Catalyst 6 was repeated to provide Catalyst 7, except that urea ($NH_2CONH_2$) was used in an amount of 20 wt %. The resultant catalytically active component had the composition of: $Mo_{10}W_2V_{3.5}Cu_1Ni_1Sr_{0.8}$ (Catalyst 7), excluding oxygen.

(Preparation of Catalyst 8)

The process described in the above Preparation of Catalyst 6 was repeated to provide Catalyst 8, except that no urea ($NH_2CONH_2$) was added before the catalyst suspension was coated onto the carrier. The resultant catalytically active component had the composition of: $Mo_{10}W_2V_{3.5}Cu_1Ni_1Sr_{0.8}$ (Catalyst 8), excluding oxygen.

The following Table 1 shows the constitutional elements and the specific surface area of each of the catalytically active components in the catalysts according to the above Preparation of Catalyst 1~ Preparation of Catalyst 8.

TABLE 1

|  | Composition | Additive amount (wt %) | Specific surface area of catalytically active component ($m^2/g$) |
|---|---|---|---|
| Catalyst 1 | $Mo_{10}Bi_{1.5}Fe_{1.2}Co_4K_{0.05}Ce_{0.1}Mn_{0.1}$ | Urea 10 | 10 |
| Catalyst 2 | $Mo_{10}Bi_{1.5}Fe_{1.2}Co_4K_{0.05}Ce_{0.1}Mn_{0.1}$ | Urea 20 | 15 |
| Catalyst 3 | $Mo_{10}Bi_{1.5}Fe_{1.2}Co_4K_{0.05}Ce_{0.1}Mn_{0.1}$ | 0 | 5 |
| Catalyst 4 | $Mo_{10}Bi_{1.5}Fe_{1.2}Co_4Al_1K_{0.05}$ | Naphthalene 10 | 9 |
| Catalyst 5 | $Mo_{10}Bi_{1.5}Fe_{1.2}Co_4Al_1K_{0.05}$ | Naphthalene 20 | 14 |
| Catalyst 6 | $Mo_{10}W_2V_{3.5}Cu_1Ni_1Sr_{0.8}$ | Urea 10 | 11 |
| Catalyst 7 | $Mo_{10}W_2V_{3.5}Cu_1Ni_1Sr_{0.8}$ | Urea 20 | 17 |
| Catalyst 8 | $Mo_{10}W_2V_{3.5}Cu_1Ni_1Sr_{0.8}$ | 0 | 8 |

(Each specific surface area of catalytically active component in Catalyst 6~Catalyst 8 was obtained by measuring the specific surface area of the catalytically active component coated on the carrier, with the exclusion of the carrier)

Example 1

To a stainless steel reactor having an inner diameter of 1 inch, Catalyst 1 was packed to the height of 1000 mm and Catalyst 2 was packed to the height of 2000 mm, from the inlet of the reaction gas toward the outlet. Then, a mixed gas containing 8 volume % of propylene, 14 volume % of oxygen, 18 volume % of water vapor and 60 volume % of inert gas was subjected to oxidation at a space velocity of 1600 hr$^{-1}$ and at a reaction temperature of 280° C.

Comparative Example 1

Oxidation was carried out in the same manner as described in Example 1, except that Catalyst 1 was packed alone to the height of 3000 mm instead of using Catalyst 1 together with Catalyst 2.

Comparative Example 2

Oxidation was carried out in the same manner as described in Example 1, except that Catalyst 2 was packed alone to the height of 3000 mm instead of using Catalyst 1 together with Catalyst 2.

Example 2

To a stainless steel reactor having an inner diameter of 1 inch, Catalyst 4 was packed to the height of 1000 mm and Catalyst 5 was packed to the height of 2000 mm, from the inlet of the reaction gas toward the outlet. Then, a mixed gas containing 8 volume % of propylene, 14 volume % of oxygen, 18 volume % of water vapor and 60 volume % of inert gas was subjected to oxidation at a space velocity of 1600 hr$^{-1}$ and at a reaction temperature of 280° C.

Comparative Example 3

Oxidation was carried out in the same manner as described in Example 2, except that Catalyst 4 was packed alone to the height of 3000 mm instead of using Catalyst 4 together with Catalyst 5.

Comparative Example 4

Oxidation was carried out in the same manner as described in Example 2, except that Catalyst 5 was packed alone to the height of 3000 mm instead of using Catalyst 4 together with Catalyst 5.

Comparative Example 5

Oxidation was carried out in the same manner as described in Example 1, except that Catalyst 3 was packed alone to the height of 3000 mm.

Example 3

To a stainless steel reactor having an inner diameter of 1 inch, Catalyst 6 was packed to the height of 1000 mm and Catalyst 7 was packed to the height of 2000 mm, from the inlet of the reaction gas toward the outlet. Then, a mixed gas containing 7 volume % of acrolein, 13 volume % of oxygen, 20 volume % of water vapor and 60 volume % of inert gas was subjected to oxidation at a space velocity of 1800 hr$^{-1}$ and at a reaction temperature of 250° C.

Comparative Example 6

Oxidation was carried out in the same manner as described in Example 3, except that Catalyst 6 was packed alone to the height of 3000 mm instead of using Catalyst 6 together with Catalyst 7.

Comparative Example 7

Oxidation was carried out in the same manner as described in Example 3, except that Catalyst 7 was packed alone to the height of 3000 mm instead of using Catalyst 6 together with Catalyst 7.

Comparative Example 8

Oxidation was carried out in the same manner as described in Example 3, except that Catalyst 8 was packed alone to the height of 3000 mm.

<Discussion 1>

The conversion ratio of reactant (propylene), selectivity and yield are calculated based on the following mathematical formulae 1~3.

propylene conversion ratio(%)=[moles of reacted propylene/moles of supplied propylene]×100    [mathematical formula 1]

selectivity(%) to acrolein+acrylic acid=[moles of produced acrolein and acrylic acid/moles of reacted propylene]×100    [mathematical formula 2]

yield(%) of acrolein+acrylic acid=[moles of produced acrolein and acrylic acid/moles of supplied propylene]×100    [mathematical formula 3]

The following Table 2 shows the results obtained from the oxidation of propylene performed by using each of the reactors packed with the catalysts according to Examples 1 and 2 and Comparative Examples 1~5.

TABLE 2

| | Catalyst | Reaction temperature (° C.) | Highest heat emission portion (° C.) | *C$_3$" conversion (%) | *AA + ACR selectivity (%) | *AA + ACR yield (%) |
|---|---|---|---|---|---|---|
| Ex. 1 | Catalyst 1 (1000 mm) + | 280 (initial) | 340 | 98.9 | 97.3 | 96.2 |
| | Catalyst 2 (2000 mm) | 290 (after 4000 h) | 348 | 98.7 | 97.4 | 96.1 |
| Comp. Ex. 1 | Catalyst 1 (3000 mm) | 280 | 340 | 95.7 | 96.7 | 92.5 |
| Comp. Ex. 2 | Catalyst 2 (3000 mm) | 270 | 359 | 99.0 | 93.9 | 93.0 |
| Ex. 2 | Catalyst 4 (1000 mm) + | 280 (initial) | 341 | 99.0 | 97.4 | 96.4 |
| | Catalyst 5 (2000 mm) | 292 (after 4000 h) | 346 | 98.9 | 97.4 | 96.3 |
| Comp. Ex. 3 | Catalyst 4 (3000 mm) | 280 | 340 | 96.0 | 96.6 | 92.7 |
| Comp. Ex. 4 | Catalyst 5 (3000 mm) | 280 | 360 | 99.2 | 94.0 | 93.2 |
| Comp. Ex. 5 | Catalyst 3 (3000 mm) | 280 | 307 | 94.8 | 96.7 | 91.7 |

*C$_3$" = propylene, ACR = acrolein, AA = acrylic acid

As shown in Table 2, Examples 1 and 2, wherein the oxidation is performed by using two kinds of catalysts having a different specific surface area of catalytically active component by virtue of the addition of a thermally decomposable or sublimable material, provide excellent conversion of the reactant (propylene) and selectivity and yield of the product, as compared to Comparative Examples 1~5, wherein the oxidation is performed by using only one kind of catalyst having the same specific surface ratio over the total catalytic layer.

<Discussion 2>

The conversion ratio of reactant (acrolein), selectivity and yield are calculated based on the following mathematical formulae 4~6.

acrolein conversion ratio(%)=[moles of reacted acrolein/moles of supplied acrolein]×100  [mathematical formula 4]

selectivity(%) to acrylic acid=[moles of produced acrylic acid/moles of reacted acrolein]×100  [mathematical formula 5]

yield(%) of acrylic acid=[moles of produced acrylic acid/moles of supplied acrolein]×100.  [mathematical formula 6]

The following Table 3 shows the results obtained from the oxidation of acrolein performed by using each of the reactors packed with the catalysts according to Example 3 and Comparative Examples 6~8.

TABLE 3

| | Catalyst | Reaction temperature (° C.) | Highest heat emission portion (° C.) | Acrolein conversion (%) | Acrylic acid selectivity (%) | Acrylic acid yield (%) |
|---|---|---|---|---|---|---|
| Ex. 3 | Catalyst 6 (1000 mm) + | 250 (initial) | 308 | 98.7 | 97.3 | 96.0 |
| | Catalyst 7 (2000 mm) | 260 (after 4000 h) | 316 | 98.5 | 97.3 | 95.8 |
| Comp. Ex. 6 | Catalyst 6 (3000 mm) | 250 | 309 | 95.5 | 96.3 | 92.0 |
| Comp. Ex. 7 | Catalyst 7 (3000 mm) | 240 | 340 | 99.5 | 93.2 | 92.7 |
| Comp. Ex. 8 | Catalyst 8 (3000 mm) | 250 | 307 | 94.8 | 96.7 | 91.7 |

As shown in Table 3, Example 3, wherein the oxidation is performed by using two kinds of catalysts having a different specific surface area of catalytically active component by virtue of the addition of a thermally decomposable or sublimable material, provide excellent conversion of acrolein and selectivity and yield of the product, as compared to Comparative Examples 6~8, wherein the oxidation is performed by using only one kind of catalyst or by using no catalyst.

INDUSTRIAL APPLICABILITY

As can be seen from the foregoing, according to the present invention, two or more kinds of catalysts, having a different specific surface of the catalytically active component due to a difference in the pore size or pore density of the catalytically active component, are packed into a reactor in such a manner that catalytic activity increases from the inlet of a reactor toward the outlet of the reactor. Therefore, (1) it is possible to efficiently control the temperature of the highest-temperature hot spot in a reactor, and thus to use a catalyst stably; and (2) it is also possible to produce unsaturated aldehydes and/or unsaturated fatty acids with high yield, by increasing the activity in the rear end part of the reaction tube. Further, it is possible to produce unsaturated aldehydes and/or unsaturated fatty acids in a stable manner even under a high concentration of starting materials, high space velocity and high load, thereby improving the productivity significantly.

The invention claimed is:

1. A shell-and-tube reactor that may be used for fixed-bed catalytic partial oxidation, the reactor being characterized by including at least one reaction zone of a first-step reaction zone for mainly producing unsaturated aldehydes from olefins and a second-step reaction zone for mainly producing unsaturated acids from unsaturated aldehydes, wherein at least one reaction zone of the above reaction zones comprises two or more catalytic layers; each of the catalytic layers is packed with a formed product of catalyst that is different in pore density and/or pore size in a catalytically active component; and the pore density and/or pore size is controlled in such a manner that specific surface area of the catalytically active component increases from the inlet of the reactor to the outlet of the reactor.

2. The shell-and-tube reactor according to claim 1, wherein the formed product of catalyst is a formed catalyst obtained by forming the catalytically active component into a desired shape, or a supported catalyst obtained by supporting the catalytically active component onto an inert carrier having a desired shape.

3. The shell-and-tube reactor according to claim 1, wherein the catalytically active component having a different pore density and/or pore size is obtained by the method comprising the steps of:
    (a) mixing metal salts forming a metal oxide, as a catalytically active component, to provide an aqueous solution or suspension of catalyst;
    (b) drying the aqueous solution or suspension of catalyst to provide catalyst powder; and
    (c) baking the resultant product obtained from the preceding step, the method further comprising a step of adding a sublimable or thermally decomposable material, having a controlled addition amount and/or a controlled particle size, during step (a) or between step (b) and step (c).

4. The shell-and-tube reactor according to claim 3, wherein the sublimable or thermally decomposable material is sublimed or decomposed at 50-200° C.

5. The shell-and-tube reactor according to claim 3, wherein the sublimable or thermally decomposable material is at least one material selected from the group consisting of urea ($NH_2CONH_2$), melamine ($C_3H_6N_6$), ammonium oxalate ($C_2H_8N_2O_4$), methyl oxalate ($C_4H_6O_4$) and naphthalene ($C_{10}H_8$).

6. The shell-and-tube reactor according to claim 3, wherein the sublimable or thermally decomposable material is present in the form of granular powder having a size of 0.01-50 μm or is present in a liquid state.

7. The shell-and-tube reactor according to claim 3, wherein the sublimable or thermally decomposable material is added in an amount of 0-30 wt % based on the weight of the catalytically active component.

8. The shell-and-tube reactor according to claim 3, wherein the catalyst powder is used after being pulverized into a size of 150 μm or less.

9. The shell-and-tube reactor according to claim 1, wherein the catalytic layer that has the smallest specific surface area of the catalytically active component by controlling the pore density and/or pore size includes the highest-temperature hot spot, and the specific surface area of the catalytically active component is 5-10 $m^2/g$.

10. The shell-and-tube reactor according to claim 1, wherein at least one reaction zone includes a first catalytic layer and a second catalytic layer, packed in two levels; the catalytically active component in the first level has a specific surface area of 5-10 $m^2/g$; and the catalytically active component in the second level has a specific surface area of 10-100 $m^2/g$.

11. The shell-and-tube reactor according to claim 1, wherein at least one reaction zone includes a first catalyst layer, a second catalytic layer and a third catalytic layer, packed in three levels; the catalytically active component in the first level has a specific surface area of 5-10 $m^2/g$; the catalytically active component in the second level has a specific surface area of 10-50 $m^2/g$; and the catalytically active component in the third level has a specific surface area of 50-100 $m^2/g$.

* * * * *